United States Patent [19]

Heimberger

[11] Patent Number: 5,349,942
[45] Date of Patent: Sep. 27, 1994

[54] FLEXIBLE ENDOSCOPE

[75] Inventor: Rudolf Heimberger, Oberderdingen, Fed. Rep. of Germany

[73] Assignee: Richard Wolf GmbH, Knittlingen, Fed. Rep. of Germany

[21] Appl. No.: 68,963

[22] Filed: May 28, 1993

[30] Foreign Application Priority Data

Jun. 6, 1992 [DE] Fed. Rep. of Germany ....... 4218706

[51] Int. Cl.5 .............................................. A61B 1/00
[52] U.S. Cl. ..................................................... 126/4
[58] Field of Search ....................... 128/4, 6, 7, 40 M; 604/95; 138/118, 120

[56] References Cited

U.S. PATENT DOCUMENTS

| 4,483,326 | 11/1984 | Yamaka et al. ............... 128/4 |
| 4,534,339 | 8/1985 | Collins et al. . |
| 4,617,914 | 10/1986 | Ueda . |
| 4,911,148 | 3/1990 | Sosnowski et al. . |

FOREIGN PATENT DOCUMENTS

| 0306723A1 | 3/1989 | European Pat. Off. . |
| 241886 | 1/1911 | Fed. Rep. of Germany . |
| WO 85/02101 | 5/1985 | PCT Int'l Appl. . |

Primary Examiner—Richard J. Apley
Assistant Examiner—Beverly A. Meindl
Attorney, Agent, or Firm—Cohen, Pontani, Lieberman, Pavane

[57] ABSTRACT

An endoscope with a flexible shaft, which consists of individual sub-assemblies releasably connected to each other. The proximal end of a flexible shaft is joined to a connecting portion and the distal end of the shaft can be steered into different positions by adjustment of an operating wire by means of an adjusting lever. The connecting portion can be coupled releasably to the distal end of the handle portion, at the proximal end of which an eyepiece portion is arranged. A hand-operated control means for the operating wire is provided in the handle portion, wherein the proximal end of the operating wire is clamped by a receiver in the control means. The receiver can be opened by operation of the adjusting lever for the purpose of releasing the above mentioned wire end, by moving the adjusting lever forwards of a neutral position. Moving the adjusting lever backwards from the neutral position effects longitudinal movement of the operating wire for controlling movement of the flexible shaft.

13 Claims, 4 Drawing Sheets

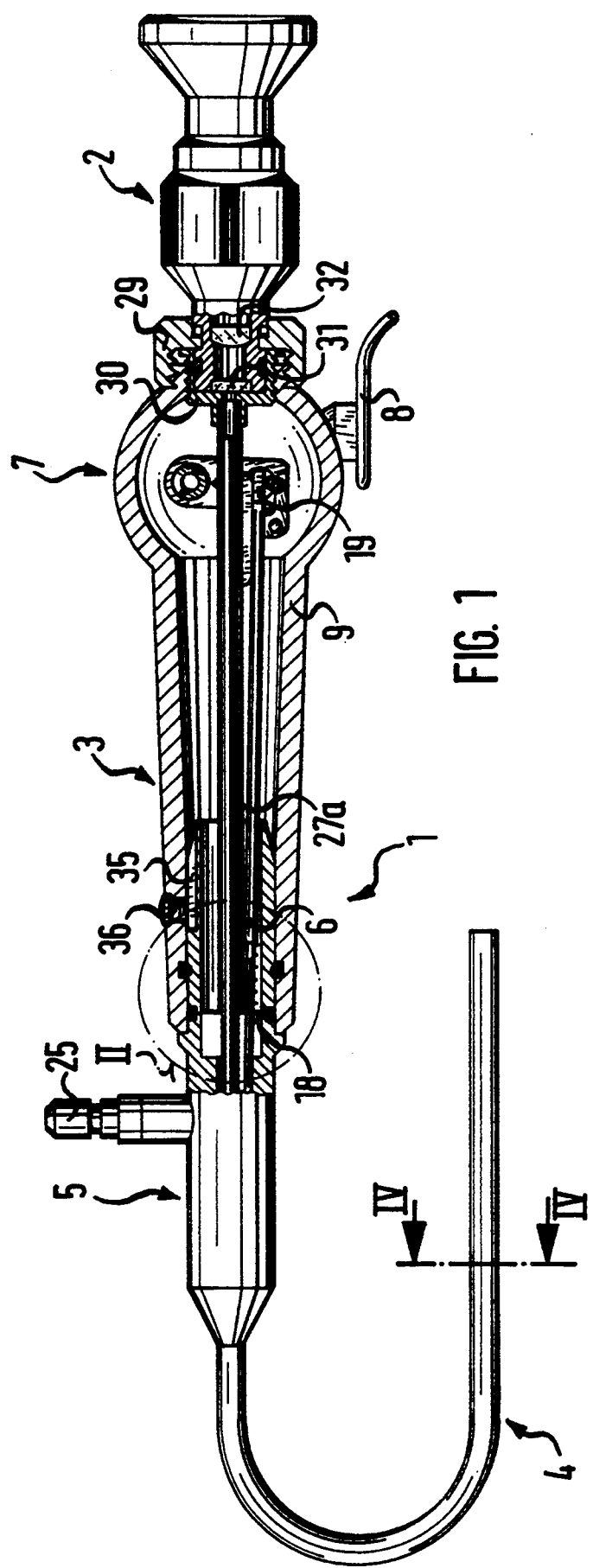
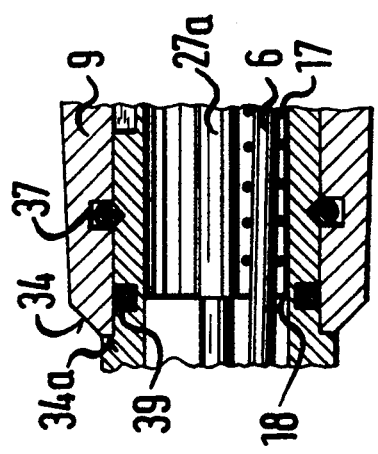
FIG. 1
FIG. 2

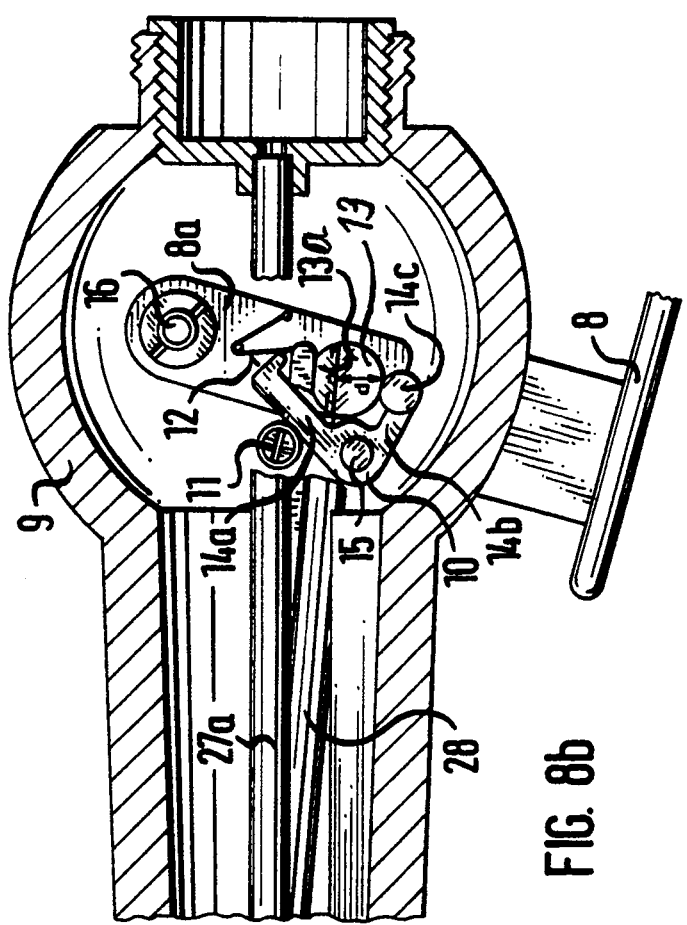
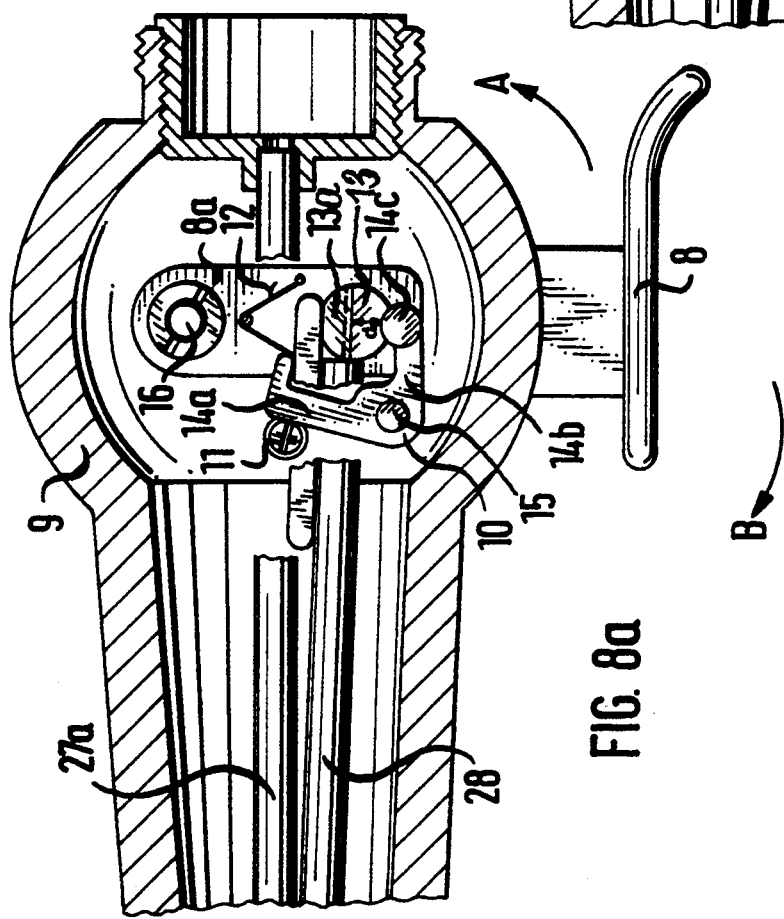
FIG. 8b
FIG. 8a

FLEXIBLE ENDOSCOPE

TECHNICAL FIELD

This invention relates to an endoscope with a flexible shaft the distal end of which can be steered into different positions by adjustment of an operating wire, and a handle to which the proximal end of the flexible shaft is releasably couplable and at the proximal end of which an eyepiece portion is provided and wherein a hand operated control means for the operating wire is provided extending into the handle portion.

BACKGROUND ART

It is known that thin flexible endoscopes with a diameter less than 2.5 mm are susceptible to damage due their delicate structure. After repeated use, image guides or light guides may break, as a result of which the flexible endoscope becomes useless. In such flexible endoscopes there must be arranged light guides for adequate illumination of the area of examination and surgery and image guides with sufficient picture elements, within a very small diameter. These are necessary in order to facilitate manipulations with accessory instruments in an area of treatment such as for example on body tissues, without endangering the patient. At least one channel for accessory instruments or for the supply and removal of fluids must also be provided. The endoscope must also enable the user to guide the distal end of the flexible shaft through body cavities or ducts e.g. blood vessels or ureters to the treatment area. This is customarily achieved by an operating wire leading to the distal end of the flexible shaft.

If, in conventional flexible endoscopes, for example a light guide or image guide is broken, then extensive repair is necessary. Sometimes this cannot even be carried out at all on account of the design of the endoscope. Therefore there has been a tendency to divide such endoscopes into individual sub-assemblies which can be replaced by sub assemblies when damage occurs.

Instruments in which the handle and the eyepiece are not designed as a structural unit, but as sub-assemblies which can be fixed together, are known. An example of this can be found in WO85/02101 which concerns a non-controllable catheter.

With flexible endoscopes it is normal to design the flexible shaft with its proximal connecting portion as a unit which can be fixed releasably to a handle rigidly connected to an eyepiece. An example of an embodiment of such an arrangement is shown in U.S. Pat. No. 4,911,148. In this endoscope one sub-assembly is formed by a flexible shaft provided with a light guide, an image guide, an instrument channel and an operating wire with a connecting portion. The second sub-assembly comprises a handle with a focusable eyepiece fixed thereto. The image guide extends beyond the proximal end of the first sub assembly and is surrounded by a sleeve which corresponds to a second sleeve in the handle portion when the endoscope is assembled. This ensnares centring of the two sub-assemblies. Very elaborate mechanics for adjustment of the operating wire are provided which means that manufacture is expensive. If for example there is damage to the eyepiece portion, then the fact that the instrument consists of only two sub-assemblies means that the whole handle/eyepiece sub-assembly must be exchanged and repaired, or even thrown away, as the eyepiece portion cannot be removed as an individual component. Furthermore control of the endoscope shaft is by turning an adjusting ring, so that handling of the instrument is not easy for the operator.

OBJECTS OF THE INVENTION

An object of the invention is to provide an endoscope which is simpler and cheaper to manufacture than prior art endoscopes and overcomes at least some of the problems referred to above. A further object is to produce a flexible endoscope which is constructed from sub-assemblies and in which three individual sub-assemblies can be easily interconnected and released and wherein control of the flexible shaft takes place by simple mechanical means to facilitate production and handling by the operator.

SUMMARY OF THE INVENTION

The object of the invention is achieved by the provision of an endoscope with a flexible shaft containing an operating wire, the proximal end of which is connected by a receiver to a control means, mounted in the endoscope's handle. The receiver can be opened by operation of an adjusting lever for the purpose of releasing the end of the operating wire.

The control means preferably includes a spring which is compressible by movement of the adjusting lever. In a neutral position of the adjusting lever the spring biases an arm in a particular direction so as to urge form locking parts of the receiver, which may included a threaded half shell, into gripping engagement with the proximal end of the operating wire. Movement of the adjusting lever towards the distal end of the handle preferably causes the arm to engage a stop pin, overcoming the spring force and thereby release the operating wire. The advantage of this solution is that in case of damage to sub-assemblies of the instrument the sub-assembly can be easily removed and repaired or replaced.

Actual control of the endoscope, i.e. deflection of the flexible distal end into different positions takes place with the same control means. The adjusting lever is moved, from the neutral position, in another direction, such as towards the proximal end of the handle so as to move the operating wire in the desired manner. The form locking arrangement between the threaded half shell of the control means and the operating wire is maintained as this occurs. The adjusting lever can thus be used not only to control the flexible shaft but also to effect release of the endoscope's sub-assemblies. Furthermore the operating wire is preferably provided with a thicker wire zone the distal end of which is movable relative to a stop located in the connecting portion against the bias of a compression spring positioned around the operating wire. If the connecting portion and the handle are accidentally fitted together when the adjusting lever is not in the forward open position, then the compression spring will be compressed thus preventing upsetting of the operating wire and damage to the threaded section located thereon.

An advantageous development of the endoscope design according to the invention lies in that, at the same time possible overloading of the control means and of the distal end of the endoscope can be avoided. Overload protection is provided by the fact that, in the case of excessive load on the operating wire, the form locking connection between the threaded section of the operating wire and the threaded half shell is released against spring pressure of the spring within the control system. Thus combined form locking and form releasing are provided by the control means.

Furthermore the instrument according to the invention is designed in such a way that the image guide of the flexible endoscope from about the middle of the connecting portion, is guided in a thin tube which serves as a protective guide tube for the image guide, and which together with the image guide protrudes far enough beyond the connecting portion in the proximal direction that when the endoscope is fully assembled the image guide and the tube end directly at a distal closure plate of the eyepiece portion. The handle is also provided with a guide tube which is designed to receive the image guide together with the tube surrounding it. The proximal end of guide tube ends immediately adjacent a stop in the handle. When the components are assembled, the closure plate of the eyepiece portion abuts against the proximal side of this stop. Advantages of such an arrangement are that on the one hand protection for the image guide is ensured and that on the other hand there are guide tubes which allow easy centering or fixing of the individual components during assembly.

Correspondingly, the operating wire is also guided from about the middle of the connecting portion in a guide tube which is fixed to the proximal end of the connecting portion. This guide tube is sufficiently long that when the endoscope is fully assembled the operating wire can co-operate reliably with the control means in the handle. In order to allow easy connection and disconnection between the connecting portion and the handle, which ensures the correct position of the individual elements, the connecting portion is provided with a longitudinal groove which corresponds to a positioning pin of the handle portion, for example designed as a ball catch.

Conveniently a round wire which latches in an annular groove of the connecting portion during assembly of the handle portion and the connecting portion is arranged at the distal end of the handle portion. The round wire is in the form an incomplete ring which sits with play in an annular groove in the handle portion. The wire is resiliently engageable with a groove in the connecting portion. With such an arrangement the connecting portion and the handle portion can easily be detached from each other.

Finally, an airtight connection of the handle portion and connecting portion can be ensured by the provision at the distal end of the handle portion of the O-ring which is arranged between the handle portion and the connection portion.

BRIEF DESCRIPTION OF THE DRAWINGS

These and other objects of the invention will become apparent from the following description of the accompanying figures which show:

FIG. 1 A complete flexible endoscope according to the invention in partial section, FIG. 2 a detail of the proximal end of the connecting portion in combination with the distal end of the handle portion, shown on a larger scale, FIG. 3 a section through the handle portion with control means designed according to the invention, FIG. 4 a cross section of the distal flexible endoscope portion through the section line IV—IV according to FIG. 1, FIG. 5 the connecting portion of the flexible endoscope in partial section, FIG. 6 an unsectioned view of the connecting portion according to FIG. 5 in a position turned through 90° relative thereto, FIG. 7 a section along the line VII—VII according to FIG. 6, and FIGS. 8a and 8b partial sections on an enlarged scale through the proximal end of the handle portion with the control means in two different positions.

Figure 3:
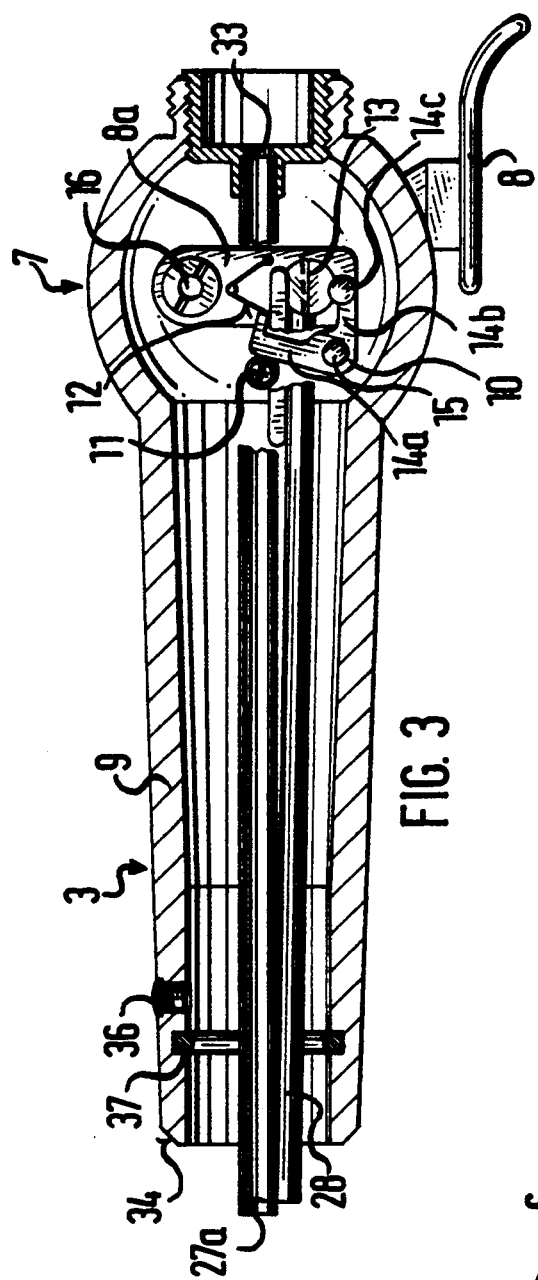

The flexible endoscope 1 according to FIG. 1 essentially consists of a focusable eyepiece portion 2, a handle portion 3 and a flexible shaft 4 with a proximal connecting portion 5 fitting into the handle portion 3. The individual sub-assemblies 2, 3 and 4/5 are, as will be described in detail below, releasably connected to each other. The control means 7 is provided within the handle portion 3. The control means 7, which is shown in FIG. 3 in the neutral position, essentially consists of an adjusting lever 8 located outside the handle housing 9, a retaining arm 10, a stop pin 11 (fixed to the housing 9), a spring 12, a threaded half shell 13, rigidly connected to the inner portion 8a of the adjusting lever 8 and comprising a jaw portion 13a which extends upwards from the remaining half shell 13. The adjusting lever 8 and its inner portion 8a are rigidly connected to each other and rotatable about a mounting shaft 16. The arm 10 can be pivoted about a mounting shaft 15 against the force of a spring 12.

Precise operation of the control means 7 in co-operation with the operating wire will be described later. First, the individual sub-assemblies and their connections with the adjacent sub-assemblies are to be described in more detail.

Figure 5:
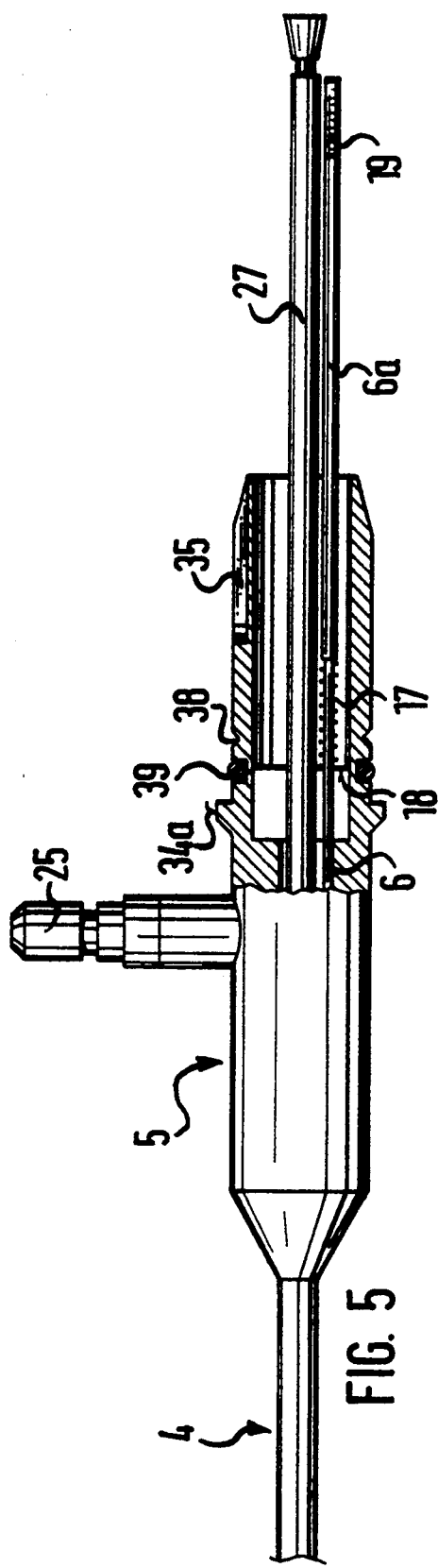

The operating wire 6, as shown in particular by FIG. 5, is movable relative to a stop 18 of the connecting portion 5. A thicker wire portion 6a is urged away from the stop 18 by a compression spring 17 located around a wire. FIG. 2 shows this section on a larger scale. In addition the operating wire 6 comprises at the proximal end a threaded section 19. If the components 3 and 5 are now accidentally fitted together with the adjusting lever 8 or the receiver 13a, 14c not in the open position, then the spring 17 is compressed and thus avoids upsetting of the operating wire 6 and damage to the section 19.

FIG. 1 shows the individual adjacent sub-assemblies of the flexible endoscope 1 in its assembled state. The focusable eyepiece portion 2, is constructed in the usual manner and therefore not described further. It is provided at its distal end with a cap nut 29. The cap nut engages a corresponding thread 30 of the proximal end of the handle portion 3. Further, the eyepiece 2 is hermetically sealed at the distal end by closure plate 31 made of light transmitting and scratch-resistant material such as sapphire. The eyepiece portion 2 is attached to the handle portion 3 with an O-ring seal 32 by means of the cap nut 29 engaging the mating counterthread 30 of the handle portion 3. This ensures a firm, air-tight and liquid-tight, releasable connection of the two endoscope sub-assemblies 2 and 3.

Figure 4:
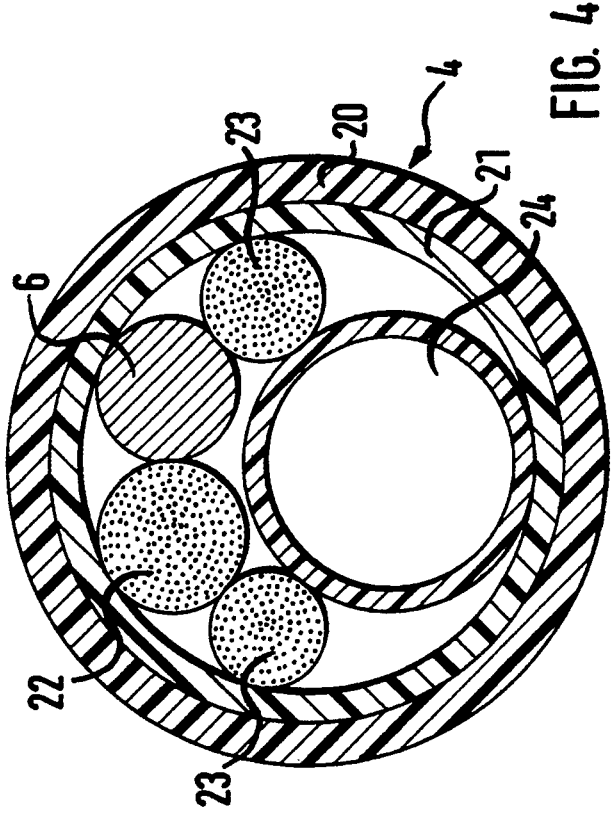

The flexible shaft 4 consists, as can be seen in particular from FIG. 4, of an inner shaft 21, which is surrounded by a casing tube 20. The inner shaft 21 can be reinforced with one or more wire coils embedded in plastic material.

The inner shaft 21 contains an image guide or an image guide bundle 22, light guides 23, the above-mentioned operating wire 6 for control purposes and a channel 24 for accessory instruments. The elements 22 to 24 can be cast e.g. in a plastics material, in a known manner in the flexible shaft 4.

Figure 6:
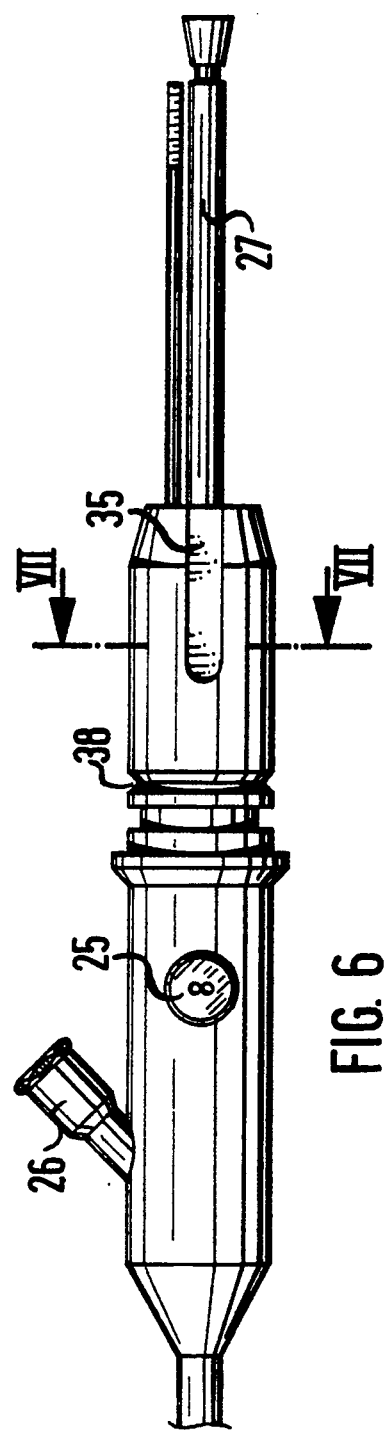
Figure 7:
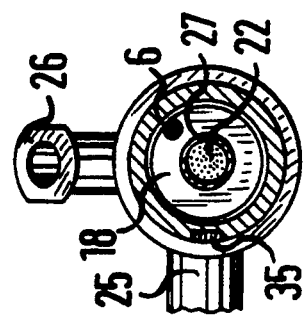

FIGS. 5 and 6 show the rigid connecting portion 5 with which the flexible shaft 4 is joined. On the connecting portion 5 is provided a connection 25 for an optical fibre cable. The light guides 23 are optically coupled to this connection. In addition the connecting portion includes an angled side fitting 26 which leads into the channel 24 for introducing accessory instruments into the flexible shaft.

The image guide or guides 22 are guided and protected from about the middle of the connecting portion 5 in a thin tube 27 which protrudes together with the image guide in the proximal direction sufficiently beyond the connecting portion 5 that when the endoscope is fully assembled according to FIG. 1, the image guide 22 and the tube 27 surrounding it, ends directly at the distal closure plate 31 of the eyepiece portion 2. In the same way the operating wire 6 is also guided from about the middle of the connecting portion 5 in a guide tube 28 which is fixed in the handle portion 3 and is sufficiently long that when the endoscope is fully assembled the operating wire 6 can co-operate reliably with the receiver 13, 13a, 14c of the control means 7.

The handle portion 3 moreover comprises a guide conduit 27a which is designed to receive the tube 27 containing the image guide 22. This guide conduit 27a ends immediately adjacent stop 33 of the handle portion 3, against the proximal side of which abuts the distal closure plate 31 of the eyepiece portion 2 when components 2 to 5 are assembled.

It is desirable to provide easy connection and release between the connecting portion 5 and the handle portion 3 which is airtight and moisture-tight and which ensures the correct position of the individual elements. The connecting portion 5 has a longitudinal groove 35 which corresponds to a positioning pin 36 of the handle portion 3, which is designed for example as a ball catch. Furthermore when the parts 3 and 5 are assembled a round wire 37 arranged at the distal end of the handle portion 3 can latch in an annular groove 38 of the connecting portion 5. So that the parts 3 and 5 can easily be detached from each other simply by pulling, the round wire 37 should be deformable and sit with sufficient play in an annular groove 38 in the handle portion. The wire is round and forms an incomplete ring. Airtightness of the connection between these two parts can be ensured by an O-ring 39 located between the handle portion 3 and the connecting portion 5.

Co-operation of the endoscope components designed according to the invention is described in more detail below.

If the connecting portion 5 is to be connected to the handle portion 3, care must be taken that the tube 27 for protection of the image guide bundles 22 and the operating wire 6 are aligned with the corresponding guide conduit 27a and tube 28 of the handle portion 3. In this position the pin 36 engages in the longitudinal groove 35 in the connecting portion 5. The adjusting lever 8 is moved in the direction B by hand to the position shown in FIG. 8b. Consequently the distance d between the jaw portion 13a of the threaded half shell 13 and counterthrust piece 14c increases. The proximal end 19 of the operating wire can now be pushed between these parts 13 and 14c which form the receiver for the proximal end 19 of the wire. At the same time the connecting portion 5 will fit into the handle portion 3. After moving the adjusting lever 8 back into the neutral position, shown in FIG. 8a form locking is provided between the wire end 19, and the receiver 13a, 14c under the influence of the spring 12. The arm part 14b of the arm 10 presses the wire end 19 from below into the threaded half shell 13 by means of the second half shell 14c. The distal end 34 of the handle housing 9 then abuts against a shoulder 34a of the connecting portion 5. As coupling of the two parts 3 and 5 takes place, the round wire 37 snap engages the annular groove 38.

Uncoupling of the operating wire 6 takes place analogously to this process. Starting from the neutral position shown in FIG. 8a, the adjusting lever 8 is pressed in the direction of arrow B to the position shown in FIG. 8b. In this position form-locking between the wire in 19 and the threaded half shell 13 is released. In this case the spring force of the spring 12 has to be overcome. The stationary stop pin 11 in this case acts on the part 14a of the arm 10 in such a way that the spring 12 is compressed. As a result the arm 10 is pivoted clockwise about the mounting shaft 15, which causes release of the wire 6. It can be seen in FIG. 8b that the distance d between the jaw portion 13a and the part 14c has increased in comparison with the neutral position shown in FIG. 8a. The handle portion 3 and the connecting portion 5 can now easily be pulled apart by overcoming the retaining force between the round wire 37 and the annular groove 38.

In the view according to FIG. 8a there is form locking between the threaded half shell 13 of the control means 7 and the end 19 of the operating wire 6. As a result the shaft 4 can be steered by moving the adjusting lever 8 in the direction of arrow A in FIG. 8a, and back in the usual manner. This causes the operating wire 6 to move back and forth in the longitudinal direction of the handle. The control means 7 at the same time projects against overloading. If the operating wire 6 is overloaded, the form-locking connection between the threaded section 19 and the threaded half shell 13 opens against the spring pressure of the spring 12, allowing the threaded half shell to ride over the threaded section 19.

Having described the invention in detail with reference to the preferred embodiment it will be apparent that modifications and variations are possible without departing from the scope of the invention defined in the appended claims

I claim:
1. Endoscope comprising:
   a flexible shaft,
   a connecting portion,
   an operating wire,
   a handle portion,
   an eyepiece portion
   a hand operated control means including a closable operating wire receiver wherein
   a distal end of said flexible shaft can be steered into different positions by adjustment of said operating wire,
   said flexible shaft is joined to said connecting portion which is releasably couplable to said handle portion,
   said eyepiece portion is arranged at the proximal end of the handle portion,
   said handle is connected to said control means which receives a proximal end of said wire by means of said receiver for operating said wire,
   and said control means further includes an adjusting lever for releasing said proximal end from said receiver.

2. Endoscope according to claim 1 wherein when said adjusting lever is in a neutral position and during adjustment of said operating wire said receiver is closed and connected in form-locking relationship to the proximal end of said wire, and said adjusting lever is movable in a particular direction to open said receiver and release said proximal end of said wire.

3. Endoscope according to claim 1 wherein said adjusting lever and an inner lever portion are rigidly connected to each other, and a retaining arm is pivotable about a mounting shaft against the force of a spring of said control means.

4. Endoscope according to claim 3 wherein starting from a neutral position during a movement of the adjustment lever in the distal direction, a stop pin of said control means acts on said arm in such a way that said spring of said control means is compressed and said receiver is opened.

5. Endoscope according to claim 1 wherein said operating wire is biased for longitudinal movement relative to a stop of said connecting portion by a compression spring located at the distal end of a thickened wire section.

6. Endoscope according to claim 5 wherein said operating wire proximally comprises a threaded section which can be brought into form-locking engagement with a threaded half shell of said receiver under the influence of a spring force.

7. Endoscope according to claim 6 wherein before overloading of said operating wire, said form locking connection between said threaded section and said threaded half shell can be released against said spring pressure of said spring of said control means.

8. Endoscope according to claim 1 wherein an image guide of said endoscope is guided from about the middle of said connecting portion in a tube.

9. Endoscope according to claim 8 wherein said handle portion comprises a guide conduit which is designed to receive said image guide accommodated in said tube and wherein said conduit ends immediately adjacent a stop of said handle portion.

10. Endoscope according to claim 9 wherein a distal closure plate of said eyepiece portion abuts against the proximal side of said stop.

11. Endoscope according to claim 1 wherein said operating wire is guided in a guide tube which can be fixed proximally in said handle portion.

12. Endoscope according to claim 1 wherein said connecting portion includes a longitudinal groove which corresponds to a positioning means of said handle portion.

13. Endoscope according to claim 1 wherein at the distal end of said handle portion a round wire is arranged which can latch in an annular groove of said connecting portion.

* * * * *